(12) United States Patent
Bracht et al.

(10) Patent No.: US 8,323,684 B2
(45) Date of Patent: Dec. 4, 2012

(54) OCCLUSIVE TRANSDERMAL THERAPEUTIC SYSTEM WITH A NON-OCCLUSIVE BACKING LAYER

(75) Inventors: Stefan Bracht, Ochtendung (DE); Christoph Schmitz, Rheinbrohl (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1678 days.

(21) Appl. No.: 10/296,802

(22) PCT Filed: May 15, 2001

(86) PCT No.: PCT/EP01/05474
§ 371 (c)(1),
(2), (4) Date: Nov. 26, 2002

(87) PCT Pub. No.: WO01/91718
PCT Pub. Date: Dec. 6, 2001

(65) Prior Publication Data
US 2003/0133970 A1  Jul. 17, 2003

(30) Foreign Application Priority Data
May 31, 2000  (DE) .................................. 100 27 258

(51) Int. Cl.
*A61F 13/00* (2006.01)
(52) U.S. Cl. ........ 424/449; 424/443; 424/445; 424/447; 424/448

(58) Field of Classification Search .................. None
See application file for complete search history.

(56) References Cited

U.S. PATENT DOCUMENTS

| | | | | |
|---|---|---|---|---|
| 4,627,852 A | | 12/1986 | Von Bittera et al. | 604/897 |
| 4,738,670 A | | 4/1988 | Von Bittera | 604/306 |
| 4,746,509 A | | 5/1988 | Haggiage et al. | 424/449 |
| 5,032,403 A | * | 7/1991 | Sinnreich | 424/448 |
| 5,230,898 A | | 7/1993 | Horstmann et al. | 424/449 |
| 5,270,358 A | * | 12/1993 | Asmus | 524/55 |
| 5,695,779 A | * | 12/1997 | Mori | 424/448 |
| 5,989,586 A | | 11/1999 | Hsu et al. | 424/449 |
| 6,582,724 B2 | * | 6/2003 | Hsu et al. | 424/449 |

FOREIGN PATENT DOCUMENTS

| | | |
|---|---|---|
| CA | 2298442 | 2/1999 |
| EP | 0 739 626 A2 | 10/1996 |
| WO | WO 00/64419 | 11/2000 |

* cited by examiner

*Primary Examiner* — Robert A Wax
*Assistant Examiner* — Hasan Ahmed
(74) *Attorney, Agent, or Firm* — Frommer Lawrence & Haug LLP

(57) ABSTRACT

The invention relates to a TTS with backing layers that guarantee a high wear comfort and that facilitate application in regions of the human body that are subject to great mechanical loads, especially the large joints of the extremities. The inventive backing layers overcome the disadvantages with respect to reduced absorption of the active substance by the skin that are typically associated with such backing layers. The inventive systems are preferably used for the local of systemic administration of anti-inflammatory and pain-relieving active substances.

21 Claims, 2 Drawing Sheets

OCCLUSIVE TRANSDERMAL THERAPEUTIC SYSTEM WITH A NON-OCCLUSIVE BACKING LAYER

Figure 1:
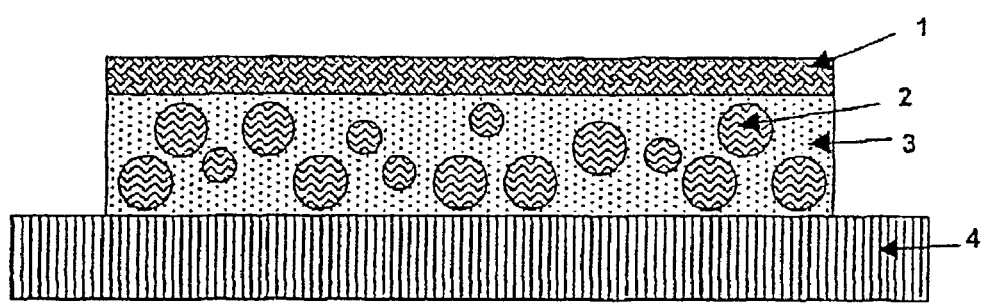

The administration of active substances through the skin is made more difficult in the majority of cases by the low permeability of the skin. Consequently it is in many cases necessary to exploit all of the possibilities available for increasing the permeability. In virtually all cases the absorption of active substances through the skin is promoted by the effect of occlusion. This refers to an accumulation of water vapor in the upper layers of the skin which develops following application of transdermal therapeutic systems (TTS) which include at least one water-vapor-impermeable layer.

The most suitable water-vapor-impermeable layer of a TTS is its backing layer. Consequently, the use of water-vapor-impermeable backing layers is state of the art and is encountered in virtually all market products.

Typically, thin polymer films of polyethylene terephthalate (PET) are used. Precisely these water vapor barrier films, however, are usually inelastic, rigid materials, with little ability to conform to the skin, which do not allow the skin surface to which the TTS is bonded to stretch or compress physiologically. Associated with this is a low level of wear comfort for the patients, especially in the case of relatively large TTS with a surface area upward of about 25 $cm^2$. To parts of the body which are under particular mechanical stress, such as the major joints of the extremities, it is virtually impossible to adhesively attach such products durably while retaining full mobility.

Finally, in the case of a TTS with a rigid backing layer of this kind, the period of wear is shortened because the lack of mechanical compatibility between elastic skin and inelastic TTS results in rapid detachment of such systems: the adhesive layer is unable to lastingly withstand the ongoing mechanical stresses. Elastic films which would be more advantageous in this respect, such as those of polyurethane or ethylene-vinyl acetate (EVA), on the other hand, possess good water vapor permeability and generate little if any occlusion.

Wovens or flag substances, finally, when used as backing layers, produce virtually no occlusion which might be of significance for the permeability of the skin.

An alternative option is to give a water vapor barrier construction to one of the other layers of the TTS, in order to be able to utilize the effect of occlusion even with a backing layer which is permeable to water vapor.

In the field of pressure-sensitive adhesive layers, formulations based on pure hydrocarbon polymers are particularly suitable for this purpose. These, however, are very lipophilic polymers, which typically possess low solvency for active pharmaceutical substances. Said substances can then frequently be embedded only in a substantially undissolved form, e.g., as a crystal dispersion, or have to be accommodated completely in an additional, differently formulated, layer.

Undissolved active substances generally result in unsatisfactory release behavior from the TTS, while additional layers complicate the construction of the system and make it more expensive.

In this respect, in accordance with the state of the art, the effect of occlusion can be used only partly or not at all in the case of TTS having an elastic backing layer, especially an elastic woven.

It is an object of the present invention, therefore to develop a transdermal therapeutic system having an elastic backing layer and an active substance layer which has water vapor barrier properties.

This object is achieved by a surprisingly uncomplicated and efficient system construction (FIG. 1).

The system of the invention is composed essentially of an adhesive layer which comprises active substance but which is configured in two phases. In the outer, water vapor barrier phase (3) an inner phase (2), which contains the active substance in dissolved form, is dispersely embedded. In conjunction with an elastic backing layer (1), preferably a woven possessing longitudinal/transverse elasticity, the result is a very thin matrix system affording excellent wear comfort while at the same time exploiting occlusion to the optimum for the increased absorption of active substance by the skin.

In accordance with standard practice, the pressure-sensitively adhering surface is masked prior to use with a redetachable protective film (4) made of conventional material, e.g., siliconized polyethylene terephthalate (PET). Suitable components for the outer and inner phases of the pressure-sensitively adhering matrix, with a view to solvent-based processing, are components which in solution produce a stable emulsion and which also form a stable two-phase system after coating and drying (removal of process solvents).

For the outer phase it is preferred to use polymers from the group of polyisobutylenes, polyisoprene, polybutenes and styrene block polymers with isoprene or butadiene. These polymers have water vapor barrier properties and are suitable as pressure sensitive adhesives when different types having different molecular weights are mixed.

The inner phase can be formed from the solution of the active substance in suitable liquid auxiliaries or else from a solution of the active substance in one or more polymers.

Dissolution in a polymer is preferential, since solutions dispersed in the form of droplets, when used as the inner phase, frequently have a tendency to be exuded or to bleed out when the droplet-containing film is subjected to mechanical stress.

Polymers suitable for the dissolution of the active substance should be compatible with the polymers specified above as being suitable for the outer phase. Compatibility in this context means that in the two-phase mixture there are particularly low interfacial energies, which are manifested in a very high degree of dispersion and a very low tendency of the emulsion to separate. Acrylate polymers and methacrylate copolymers and ethyl-vinyl acetate copolymers have proven highly compatible in this sense. In the case of the (meth) acrylate copolymers, the polymers may also in turn be pressure-sensitively adhering. The result in that case is a layer, embedded into an outer pressure-sensitive adhesive phase comprising hydrocarbon polymers, which is substantially uniform in terms of its viscoelastic properties, something which may have a positive effect on the wear properties on the skin. Among the (meth)acrylate copolymers, those types which contain free carboxyl groups may be of advantage. By neutralizing these groups with suitable alkaline auxiliaries, e.g., potassium hydroxide, it is possible to tailor the hydrophilic/lipophilic balance of such polymers. This may be advantageous for establishing a stable emulsion in a mixture with hydrocarbon polymers. Appropriate active substances are, in particular, non-steroidal antiphlogistics (in German, NSAR for non-steroidal antirheumatics; in English, NSAID for non-steroidal antiinflammatory drugs). These active substances are frequently applied locally, externally, in the region of joints, especially those of the extremities. It is precisely at these application sites, subject to high mechanical stress, that the TTS of the invention prove particularly advantageous. With no claim to completeness, the active substances in question are those from the group of diclofenac or one of its pharmaceutically acceptable salts, preferably the sodium salt, ibuprofen, ketoprofen, fluriprofen, etofenamate, hydroxyethyl salicylate, meloxicam, piroxicam, lornoxicam, tenoxicam or indomethacin.

Besides the polymers for the outer phase, polymers for the inner phase, where appropriate, and the active pharmaceutical substance, numerous other auxiliaries may be employed as well, such as are known to those skilled in the art for use in TTS.

Thus it is possible, for example, to use permeation enhancers, preferably in the inner phase of the matrix. Suitable permeation enhancers include compounds from the group of low molecular mass monohydric or polyhydric alcohols, fatty acids (preferably oleic acid), fatty alcohols, fatty alcohol ethers, polyoxyethylated fatty alcohols, fatty acid esters (especially monoglycerides and monoesters with propylene glycol), sorbitan fatty acid esters, and polyoxyethylated sorbitan fatty acid esters, and also dimethylisosorbitol.

Also suitable are surfactants which have the capacity to exert a positive influence on the stability of the two-phase matrix layer by lowering the interfacial energy.

Suitable elastic, water-vapor-permeable backing layers include films of polyurethane or ethyl-vinyl acetate copolymers. Particularly suitable, however, are wovens or non-woven flag materials, or composites of such materials. Examples of suitable materials here include cotton, cellulose, viscose, polyurethane or poly-ethylene terephthalate (PET).

Very particular suitability is possessed by PET wovens possessing longitudinal and transverse elasticity.

EXAMPLE 1

The transdermal therapeutic system of the invention possesses the following structure and composition (% by weight):

| Inner phase: | |
| --- | --- |
| Ketoprofen | 4.00% |
| Oleic acid | 4.00% |
| Potassium hydroxide | 0.53% |
| Aluminum ions | 0.008% |
| Durotak 387-2353 | 11.4% |
| Outer phase: | |
| Oppanol B10 | 60.0% |
| Oppanol B100 | 20.0% |

The backing layer used is a bielastic PET woven.

EXAMPLE 2

Comparative Example

The transdermal therapeutic system with the standard one-phase structure has the following composition (% by weight):

| Ketoprofen | 10.00% |
| --- | --- |
| Oleic acid | 18.00% |
| Durotak 387-2052 | 72.00% |

The backing layer used is the same longitudinally and transversely elastic PET woven as for the inventive Example 1.

For production, ketoprofen and oleic acid are homogeneously dissolved or distributed in the solution of Durotak (National Starch & Chemical) adhesive by stirred incorporation. The one-phase solution obtained is coated onto a redetachable backing film of siliconized polyethylene terephthalate (PET, thickness: 100 μm) and dried at 80° C. in an air-exhaust oven for 10 minutes. The target weight per unit area of the dried adhesive film is 80 g/m².

The dried adhesive film is laminated with a longitudinally and transversely elastic PET woven (100 g/m² basis weight).

Figure 2:
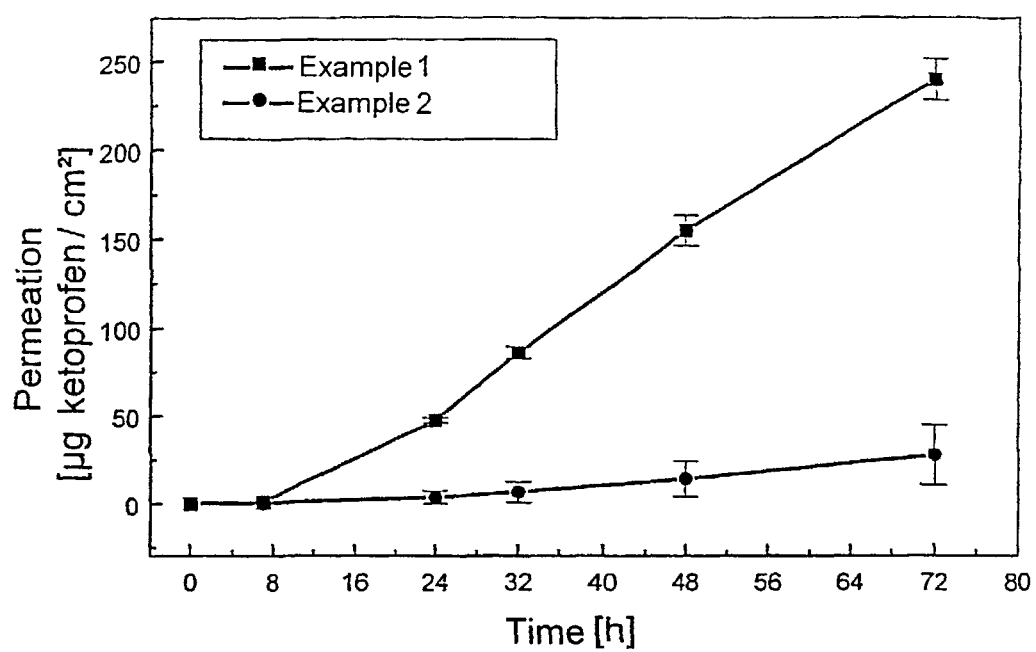

FIG. 2 shows in the form of a graph a comparison of the permeation of active substance on human skin in vitro (full skin thickness, n=3, experiments with skin from the same donor). The TTS produced in accordance with the inventive Example 1 achieves very much higher release rates than a conventional TTS produced in accordance with Example 2, despite the fact that the overall amount of active substance (ketoprofen) made available is in fact considerably lower in the inventive TTS than in the comparative TTS.

The invention claimed is:

1. An occlusive transdermal therapeutic system comprising:
   a water-vapor-permeable and air-permeable elastic backing layer,
   a matrix layer comprising a non-steroidal anti-inflammatory drug, optionally one or more auxiliaries, and optionally one or more permeation enhancers, and
   a redetachable protective layer,
   wherein the matrix layer is present in two phases, wherein
   (i) the first phase is an outer phase comprising one or more hydrocarbon polymers and which is substantially impermeable to water vapor and air, and
   (ii) the second phase is an inner phase which forms a dispersion in said first phase and which contain the one or more non-steroidal anti-inflammatory drug in dissolved form, wherein the second phase comprises of one or more polymers selected from the group consisting of acrylate copolymers, methacrylate copolymers, ethylene vinyl acetate copolymers and mixtures thereof and wherein the dispersion has a droplet diameter of 10 nm to 10 μm.

2. The occlusive transdermal therapeutic system of claim 1, wherein the elastic backing layer is composed of a longitudinally and transversely elastic woven.

3. The occlusive transdermal therapeutic system of claim 2, wherein the woven is composed of polyethylene terephthalate (PET).

4. The occlusive transdermal therapeutic system of claim 3, wherein:
   the one or more non-steroidal anti-inflammatory drug is selected from the group consisting of diclofenac, a pharmaceutically acceptable salt of diclofenac, ibuprofen, ketoprofen, flurbiprofen, etofenamate, hydroxyethyl salicylate, meloxicam, piroxicam, lornoxicam, tenoxicam, indomethacin, and mixtures thereof
   the outer phase of the matrix is composed of one or more polymers selected from the group consisting of polyisobutylenes, polyisoprene, polybutenes, a styrene block polymer with isoprene, a styrene block copolymer with butadiene and mixtures thereof; and
   the inner phase of the matrix is composed of one or more polymers selected from the group consisting of acrylate copolymers, methacrylate copolymers, ethylene vinyl acetate copolymers and mixtures thereof.

5. The occlusive transdermal therapeutic system of claim 4, wherein:
   the fraction of the inner phase of the matrix is 10-25% by weight of the matrix comprising active substance;

the dispersion has a droplet diameter of from 100 nm to 1 µm; and contains one or more permeation enhancers in the inner phase of the matrix and which are low molecular mass monohydric or polyhydric alcohols, fatty acids, fatty alcohols, fatty alcohol ethers, polyoxyethylated fatty alcohols, fatty acid esters, sorbitan fatty acid esters, polyoxyethylated sorbitan fatty acid esters and/or dimethylisosorbitol.

6. The occlusive transdermal therapeutic system of claim 5, wherein the one or more non-steroidal anti-inflammatory drug is in solution in suitable liquid auxiliaries or in one or more polymers.

7. The occlusive transdermal therapeutic system of claim 1, wherein the outer phase of the matrix is composed of one or more polymers selected from the group consisting of polyisobutylenes, polyisoprene, polybutenes, a styrene block polymer with isoprene, a styrene block polymer with butadiene and mixtures thereof.

8. The occlusive transdermal therapeutic system of claim 6, wherein the outer phase of the matrix is composed of polyisobutylenes of at least two different molecular weights.

9. The occlusive transdermal therapeutic system of claim 1, wherein in the case of acrylate or methacylate copolymers the polymers in question are carboxyl-containing polymers.

10. The occlusive transdermal therapeutic system of claim 1, wherein the inner phase of the matrix is free from polymers and contains the one or more non-steroidal anti-inflammatory drug in solution in at least one liquid auxiliary.

11. The occlusive transdermal therapeutic system of claim 1, wherein the fraction of the inner phase of the matrix is 5-40% by weight.

12. The occlusive transdermal therapeutic system of claim 1, wherein the matrix comprising the one or more non-steroidal anti-inflammatory drug amounts to a layer thickness of 60-200 g/m².

13. The occlusive transdermal therapeutic system of claim 1, wherein the one or more non-steroidal anti-inflammatory drug is selected from the group consisting of diclofenac, a pharmaceutically acceptable salt of diclofenac, ibuprofen, ketoprofen, flurbiprofen, etofenamate, hydroxyethyl salicylate, meloxicam, piroxicam, lornoxicam, tenoxicam, indomethacin, and mixtures thereof.

14. The occlusive transdermal therapeutic system of claim 1, wherein the one or more non-steroidal anti-inflammatory drug is present in the inner phase of the matrix in a concentration range of 50-150% by weight of the saturation solubility of the one or more non-steroidal anti-inflammatory drug.

15. The occlusive transdermal therapeutic system of claim 5, wherein the outer phase of the matrix is composed of polyisobutylenes of three different molecular weights.

16. The occlusive transdermal therapeutic system of claim 1, wherein the system comprises at least one permeation enhance which is low molecular mass monohydric or polyhydric alcohols, fatty acids, fatty alcohols, fatty alcohol ethers, polyoxyethylated fatty alcohols, fatty acid esters, sorbitan fatty acid esters, polyoxyethylated sorbitan fatty acid esters and/or dimethylisosorbitol.

17. The occlusive transdermal therapeutic system of claim 8, wherein the outer phase of the matrix is composed of polyisobutylenes of three different molecular weights.

18. The occlusive transdermal therapeutic system of claim 11, wherein the fraction of the inner phase of the matrix is 10-25% by weight of the matrix comprising active substance.

19. The occlusive transdermal therapeutic system of claim 12, wherein the matrix comprising the one or more non-steroidal anti-inflammatory drug amounts to a layer thickness of 80-120 g/m².

20. The occlusive transdermal therapeutic system of claim 1, wherein the inner phase forms a dispersion in the outer phase of the matrix, with a droplet diameter of from 100 nm to 1 µm.

21. The occlusive transdermal therapeutic system of claim 15, wherein the at least one permeation enhancer is in the inner phase of the matrix.

* * * * *